US011130723B2

(12) United States Patent
Kudo et al.

(10) Patent No.: US 11,130,723 B2
(45) Date of Patent: Sep. 28, 2021

(54) CARBON DIOXIDE ELECTROLYTIC DEVICE

(71) Applicant: KABUSHIKI KAISHA TOSHIBA, Minato-ku (JP)

(72) Inventors: Yuki Kudo, Yokohama (JP); Akihiko Ono, Kita (JP); Masakazu Yamagiwa, Yokohama (JP); Eishi Tsutsumi, Kawasaki (JP); Yoshitsune Sugano, Kawasaki (JP); Ryota Kitagawa, Setagaya (JP); Jun Tamura, Chuo (JP); Satoshi Mikoshiba, Yamato (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 16/830,708

(22) Filed: Mar. 26, 2020

(65) Prior Publication Data

US 2020/0223775 A1 Jul. 16, 2020

Related U.S. Application Data

(63) Continuation of application No. 15/698,329, filed on Sep. 7, 2017.

(30) Foreign Application Priority Data

Mar. 14, 2017 (JP) .................................. 2017-048928

(51) Int. Cl.
*C25B 3/00* (2021.01)
*C07C 29/153* (2006.01)
(Continued)

(52) U.S. Cl.
CPC .............. *C07C 29/153* (2013.01); *C25B 1/00* (2013.01); *C25B 1/04* (2013.01); *C25B 3/25* (2021.01);
(Continued)

(58) Field of Classification Search
CPC .... C25B 3/04; C25B 3/02; C25B 3/00; C25B 9/08; C25B 9/00; C25B 11/00; C25B 11/035; C25B 1/04
See application file for complete search history.

(56) References Cited

U.S. PATENT DOCUMENTS 9,255,335 B2 2/2016 Kanan et al.
2008/0223727 A1 9/2008 Oloman et al.
(Continued)

FOREIGN PATENT DOCUMENTS

DE 10 2015 201 132 A1 7/2016
JP 2009-511740 3/2009
(Continued)

OTHER PUBLICATIONS

Charles Delacourt, et al. "Design of an Electrochemical Cell Making Syngas (Co + $H_2$) from $CO_2$ and $H_2O$ Reduction at Room Temperature", Journal of the Electrochemical Society, 155 (1), 2008, 8 pages.

(Continued)

*Primary Examiner* — Zulmariam Mendez
(74) *Attorney, Agent, or Firm* — Oblon, McClelland, Maier & Neustadt, L.L.P.

(57) ABSTRACT

A carbon dioxide electrolytic device of an embodiment includes: an anode part including an anode which oxidizes water or hydroxide ions to produce oxygen; a cathode part including a cathode which reduces carbon dioxide to produce a carbon compound, a cathode solution flow path which supplies a cathode solution to the cathode, and a gas flow path which supplies carbon dioxide to the cathode; a separator which separates the anode part and the cathode part; and a differential pressure control unit which controls a differential pressure between a pressure of the cathode solution and a pressure of the carbon dioxide so as to adjust (Continued)

a production amount of the carbon dioxide produced by a reduction reaction in the cathode part.

7 Claims, 8 Drawing Sheets

(51) Int. Cl.
    *C25B 15/02*     (2021.01)
    *C25B 1/00*     (2021.01)
    *C25B 1/04*     (2021.01)
    *C25B 3/25*     (2021.01)
    *C25B 9/19*     (2021.01)
    *C25B 9/73*     (2021.01)

(52) U.S. Cl.
    CPC .................. *C25B 9/19* (2021.01); *C25B 9/73* (2021.01); *C25B 15/02* (2013.01); *Y02E 60/36* (2013.01)

(56) References Cited

U.S. PATENT DOCUMENTS

| | | |
|---|---|---|
| 2011/0132770 A1 | 6/2011 | Sala et al. |
| 2013/0186771 A1 | 7/2013 | Zhai et al. |
| 2014/0326611 A1 | 11/2014 | Yan et al. |
| 2016/0145752 A1 | 5/2016 | Salehi et al. |

FOREIGN PATENT DOCUMENTS

| | | |
|---|---|---|
| JP | 2011-521104 | 7/2011 |
| JP | 2013-544957 | 12/2013 |
| WO | WO 2016/134952 A1 | 9/2016 |
| WO | WO 2017/025285 A1 | 2/2017 |

OTHER PUBLICATIONS

Sichao MA, et al. "Efficient Electrochemical Flow System with Improved Anode for the Conversion of $CO_2$ to CO", Journal of The Electrochemical Society, 161 (10), 2014, 8 pages.

Extended European Search Report dated Feb. 20, 2018 in European Patent Application No. 17189579.0, 9 pages.

B. Endrödi, et al., "Continuous-flow Electroreduction of Carbon Dioxide", Progress in Energy and Combustion Science, XP085135284, vol. 62, Jun. 13, 2017, pp. 133-154.

CARBON DIOXIDE ELECTROLYTIC DEVICE

CROSS REFERENCE TO RELATED APPLICATION

This application is a continuation application of U.S. application Ser. No. 15/698,329 filed Sep. 7, 2017, pending and incorporated by reference herein and claims the benefit of priority from Japanese Patent Application No. 2017-048928, filed on Mar. 14, 2017; the entire contents of which are incorporated herein by reference.

FIELD

Embodiments described herein relate generally to a carbon dioxide electrolytic device.

BACKGROUND

In recent years, there has been a concern for depletion of fossil fuel such as petroleum or coal, and expectation for sustainably-usable renewable energy has been rising. As the renewable energy, a solar cell, wind power generation, and the like can be cited. Because these depend on weather and a natural situation in a power generation amount, there is a problem that stable supply of electric power is difficult. Therefore, there has been made an attempt to store the electric power generated by the renewable energy in a storage battery and stabilize the electric power. However, when the electric power is stored, there are problems that a cost is required for the storage battery and a loss occurs at a time of storage.

For such points, attention is being given to a technology of performing water electrolysis using the electric power generated by the renewable energy to produce hydrogen ($H_2$) from water or reducing carbon dioxide ($CO_2$) electrochemically to convert it into a chemical substance (chemical energy) such as a carbon compound such as carbon monoxide (CO), a formic acid (HCOOH), methanol ($CH_3OH$), methane ($CH_4$), an acetic acid ($CH_3COOH$), ethanol ($C_2H_5OH$), ethane ($C_2H_6$), or ethylene ($C_2H_4$). When these chemical substances are stored in a cylinder or a tank, as compared with when the electric power (electric energy) is stored in the storage battery, there are advantages that a storage cost of energy can be reduced and a storage loss is also small.

As a configuration of a carbon dioxide electrolytic device, for example, three configurations indicated below are being studied. As a first configuration, there can be cited a configuration which includes an electrolytic bath accommodating an electrolytic solution in which carbon dioxide ($CO_2$) has been absorbed, an anode (oxidation electrode) and a cathode (reduction electrode) immersed in the electrolytic solution, and a separator such as an ion exchange membrane disposed so as to separate the anode and the cathode. As a second configuration, there can be cited a configuration which includes a cathode solution flow path disposed along one surface of a cathode, a $CO_2$ gas flow path disposed along the other surface of the cathode, an anode solution flow path disposed along one surface of an anode, and a separator disposed between the cathode solution flow path and the anode solution flow path. As a third configuration, similarly to a solid polymer fuel cell, there can be cited a configuration in which an ion exchange membrane is disposed between an anode and a cathode and a $CO_2$ gas flow path is disposed along the other surface of the cathode.

Among the above-described configuration examples of the carbon dioxide electrolytic device, in the first configuration example, in an electrolysis operation at about 10 $mA/cm^2$ or more, an overvoltage loss is large, resulting in a large cell voltage, and therefore there is a problem that electrolysis efficiency at a high current density is low. In the second configuration example, a cell voltage can be reduced more than that in the first configuration example, and the electrolysis efficiency can be improved. However, there is a problem that selectivity of a product to be obtained by a reduction reaction on a cathode side is low and variations exist in the electrolysis efficiency in the second configuration example. Note that in the third configuration example, development, selection, and the like of an ion exchange membrane suitable for electrolysis of $CO_2$ are required.

DETAILED DESCRIPTION

According to the embodiments of the present invention, there is provided a carbon dioxide electrolytic device that includes: a cathode part including a cathode to reduce carbon dioxide and thus produce a carbon compound, a cathode solution flow path to supply a cathode solution to the cathode, and a gas flow path to supply carbon dioxide to the cathode; an anode part including an anode to oxidize water or hydroxide ions and thus produce oxygen and an anode solution flow path to supply an anode solution to the anode; a separator to separate the anode part and the cathode part; a power supply to pass an electric current between the anode and the cathode; a first pressure control unit to control a pressure of the cathode solution flowing in the cathode solution flow path; a second pressure control unit to control a pressure of the carbon dioxide flowing in the gas flow path; a detection unit to detect a production amount of the carbon compound produced by a reduction reaction in the cathode part; and a differential pressure control unit to control a differential pressure between a pressure of the cathode solution and a pressure of the carbon dioxide so as to adjust the production amount of the carbon compound detected in the detection unit.

Hereinafter, a carbon dioxide electrolytic device of an embodiment will be described with reference to the drawings. In the embodiment presented below, substantially the same components are denoted by the same reference signs, and a description thereof is sometimes partially omitted. The drawings are schematic, and a relationship between a thickness and a planar size, thickness proportions of the respective portions, and the like are sometimes different from actual ones.

Figure 1:
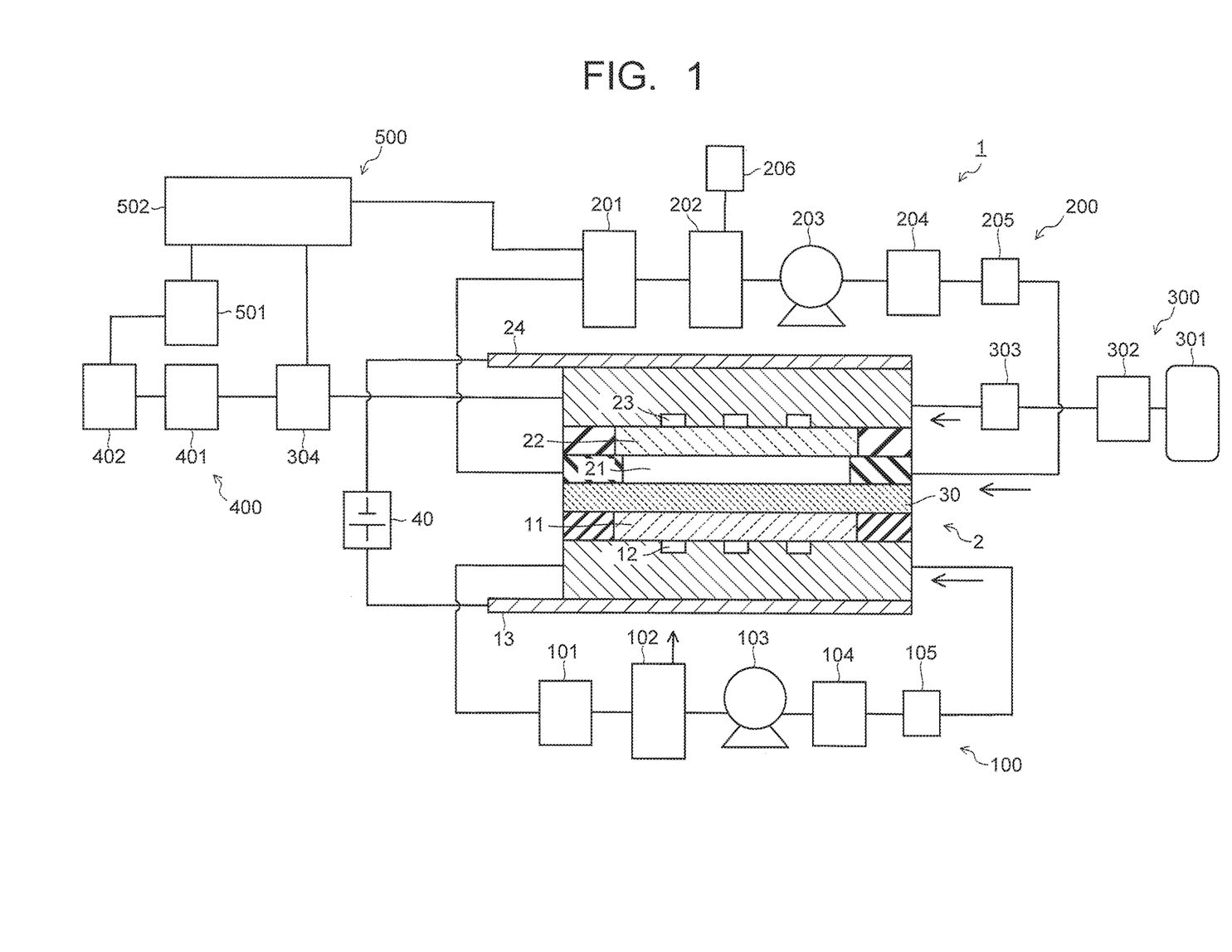
FIG. 1 is a view illustrating a carbon dioxide electrolytic device of an embodiment.
Figure 2:
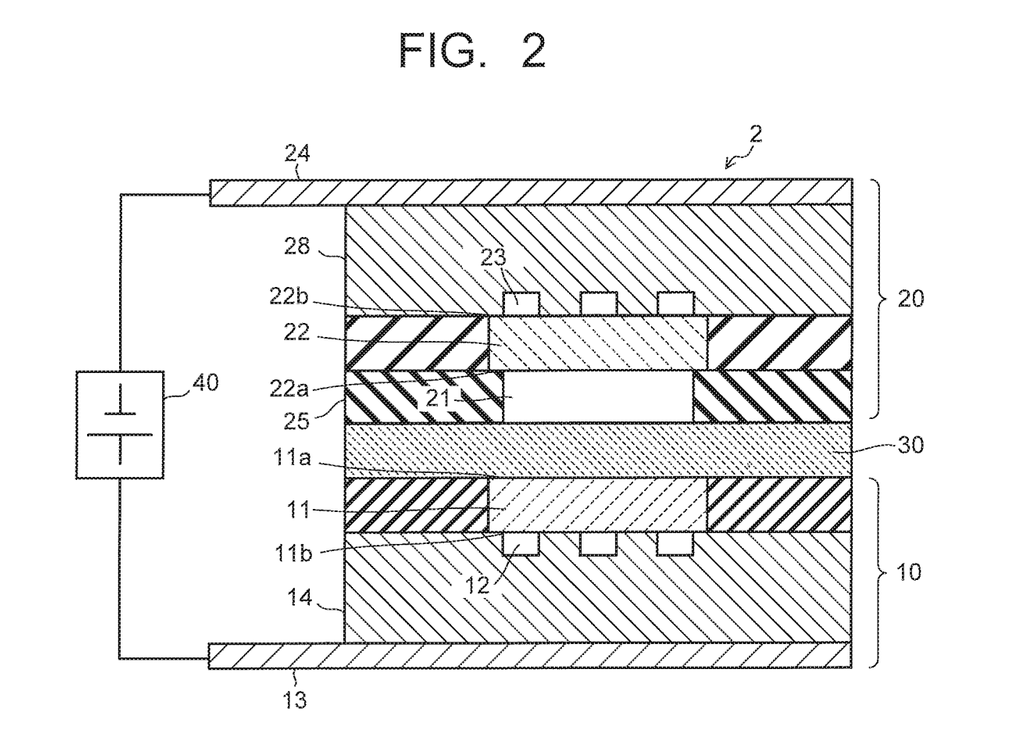
FIG. 2 is a sectional view illustrating an electrolysis cell of the carbon dioxide electrolytic device illustrated in FIG. 1.

FIG. 1 is a view illustrating a configuration of a carbon dioxide electrolytic device according to the embodiment. FIG. 2 is a sectional view illustrating a configuration of an electrolysis cell in the electrolytic device illustrated in FIG. 1. A carbon dioxide electrolytic device 1 illustrated in FIG. 1 includes: an electrolysis cell 2; an anode solution supply system 100 which supplies an anode solution to the electrolysis cell 2; a cathode solution supply system 200 which supplies a cathode solution to the electrolysis cell 2; a gas supply system 300 which supplies carbon dioxide ($CO_2$) gas to the electrolysis cell 2; a product collection system 400 which collects a product produced by a reduction reaction in the electrolysis cell and a product control system 500 which detects a type and a production amount of the collected product and controls the product.

The electrolysis cell 2 includes an anode part 10, a cathode part 20, and a separator 30 as illustrated in FIG. 2. The anode part 10 includes an anode 11, an anode solution flow path 12, and an anode current collector 13. The cathode part 20 includes a cathode solution flow path 21, a cathode 22, a $CO_2$ gas flow path 23, and a cathode current collector 24. The separator 30 is disposed so as to separate the anode part 10 and the cathode part 20. The electrolysis cell 2 is sandwiched by a pair of support plates not illustrated, and further tightened by bolts or the like. In FIG. 1 and FIG. 2, a reference sign 40 is a power supply which passes an electric current through the anode 11 and the cathode 22. The power supply 40 is connected via a current introduction member to the anode 11 and the cathode 22. The power supply 40 is not limited to a normal commercial power supply, battery, or the like, and may supply electric power generated by renewable energy such as a solar cell or wind power generation.

The anode 11 is an electrode (oxidation electrode) which causes an oxidation reaction of water ($H_2O$) in an anode solution to produce oxygen ($O_2$) or hydrogen ions ($H^+$), or causes an oxidation reaction of hydroxide ions ($OH^-$) produced in the cathode part 20 to produce oxygen ($O_2$) or water ($H_2O$). The anode 11 preferably has a first surface 11a in contact with the separator 30 and a second surface 11b facing the anode solution flow path 12. The first surface 11a of the anode 11 is in close contact with the separator 30. The anode solution flow path 12 supplies the anode solution to the anode 11, and is constituted by a pit (groove portion/concave portion) provided in a first flow path plate 14. The anode solution flows through in the anode solution flow path 12 so as to be in contact with the anode 11. The anode current collector 13 is electrically in contact with a surface on a side opposite to the anode 11 of the first flow path plate 14 constituting the anode solution flow path 12.

Figure 3:
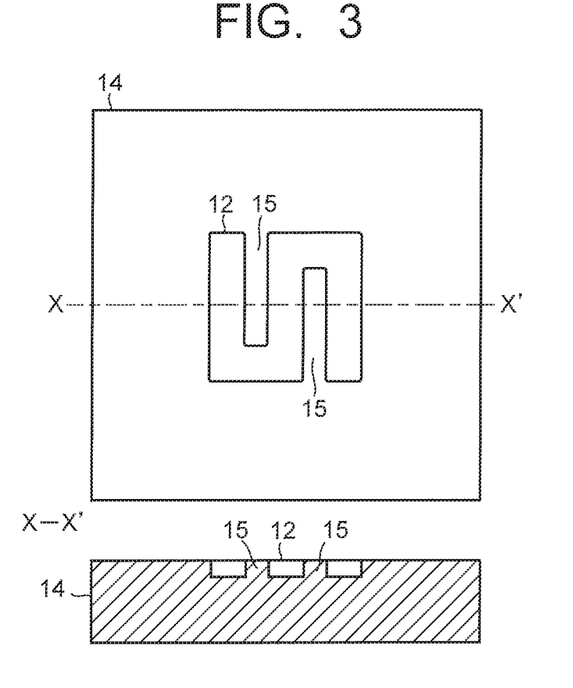
FIG. 3 is a view illustrating one example of an anode solution flow path in the electrolysis cell illustrated in FIG. 2.

To the first flow path plate 14, a solution inlet port and a solution outlet port whose illustrations are omitted are connected, and via these solution inlet port and solution outlet port, the anode solution is introduced and discharged by the anode solution supply system 100. For the first flow path plate 14, a material having low chemical reactivity and high conductivity is preferably used. As such a material, a metal material such as Ti or SUS, carbon, or the like can be cited. Along the anode solution flow path 12, as illustrated in FIG. 3, a plurality of lands (convex potions) 15 are preferably provided. The lands 15 are provided for mechanical retention and electrical continuity. The lands 15 are preferably provided alternately to uniformize flow of the anode solution. The above lands 15 make the anode solution flow path 12 serpentine. Moreover, also for a good discharge of the anode solution in which oxygen ($O_2$) gas is mixed, the lands 15 are preferably provided alternately along the anode solution flow path 12 to make the anode solution flow path 12 serpentine.

The anode 11 is preferably mainly constituted of a catalyst material (anode catalyst material) capable of oxidizing water ($H_2O$) to produce oxygen or hydrogen ions or oxidizing hydroxide ions ($OH^-$) to produce water or oxygen, and capable of reducing an overvoltage of the above reaction. As such a catalyst material, there can be cited a metal such as platinum (Pt), palladium (Pd), or nickel (Ni), an alloy or an intermetallic compound containing the above metals, a binary metal oxide such as a manganese oxide (Mn—O), an iridium oxide (Ir—O), a nickel oxide (Ni—O), a cobalt oxide (Co—O), an iron oxide (Fe—O), a tin oxide (Sn—O), an indium oxide (In—O), a ruthenium oxide (Ru—O), a lithium oxide (Li—O), or a lanthanum oxide (La—O), a ternary metal oxide such as Ni—Co—O, Ni—Fe—O, La—Co—O, Ni—La—O, or Sr—Fe—O, a quaternary metal oxide such as Pb—Ru—Ir—O or La—Sr—Co—O, or a metal complex such as a Ru complex or a Fe complex.

The anode 11 includes a base material having a structure capable of moving the anode solution or ions between the separator 30 and the anode solution flow path 12, for example, a porous structure such as a mesh material, a punching material, a porous body, or a metal fiber sintered body. The base material may be constituted of a metal such as titanium (Ti), nickel (Ni), or iron (Fe), or a metal material such as an alloy (for example, SUS) containing at least one of these metals, or may be constituted of the above-described anode catalyst material. When the oxide is used as the anode catalyst material, the anode catalyst material preferably adheres to or is stacked on a surface of the base material constituted of the above-described metal material to form a catalyst layer. The anode catalyst material preferably has nanoparticle, a nanostructure, a nanowire, or the like for the purpose of increasing the oxidation reaction. The nanostructure is a structure in which nanoscale irregularities are formed on a surface of the catalyst material.

The cathode 22 is an electrode (reduction electrode) which causes a reduction reaction of carbon dioxide ($CO_2$) or a reduction reaction of a carbon compound produced thereby to produce a carbon compound such as carbon monoxide (CO), methane ($CH_4$), ethane ($C_2H_6$), ethylene ($C_2H_4$), methanol ($CH_3OH$), ethanol ($C_2H_5OH$), or ethylene glycol ($C_2H_6O_2$). In the cathode 22, simultaneously with the reduction reaction of carbon dioxide ($CO_2$), a side reaction in which hydrogen ($H_2$) is produced by a reduction reaction of water ($H_2O$) is sometimes caused. The cathode 22 has a first surface 22a facing the cathode solution flow path 21 and a second surface 22b facing the $CO_2$ gas flow path 23. The cathode solution flow path 21 is disposed between the cathode 22 and the separator 30 so that the cathode solution is in contact with the cathode 22 and the separator 30.

The cathode solution flow path 21 is constituted by an opening portion provided in a second flow path plate 25. To the second flow path plate 25, a solution inlet port and a solution outlet port whose illustrations are omitted are connected, and via these solution inlet port and solution outlet port, the cathode solution is introduced and discharged by the cathode solution supply system 200. The cathode solution flows through in the cathode solution flow path 21 so as to be in contact with the cathode 22 and the separator 30. For the second flow path plate 25 constituting the cathode solution flow path 21, a material having low chemical reactivity and having no conductivity is preferably used. As such a material, there can be cited an insulating resin material such as an acrylic resin, polyetheretherketone (PEEK), or a fluorocarbon resin.

Figure 4:
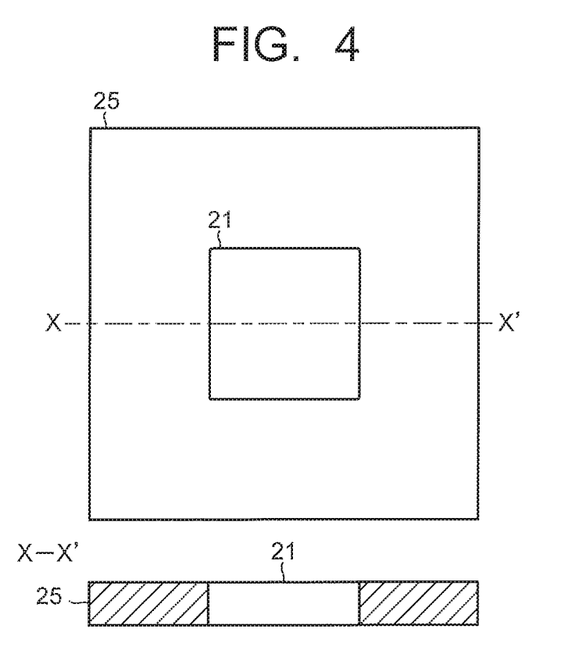
FIG. 4 is a view illustrating one example of a cathode solution flow path in the electrolysis cell illustrated in FIG. 2.
Figure 5:
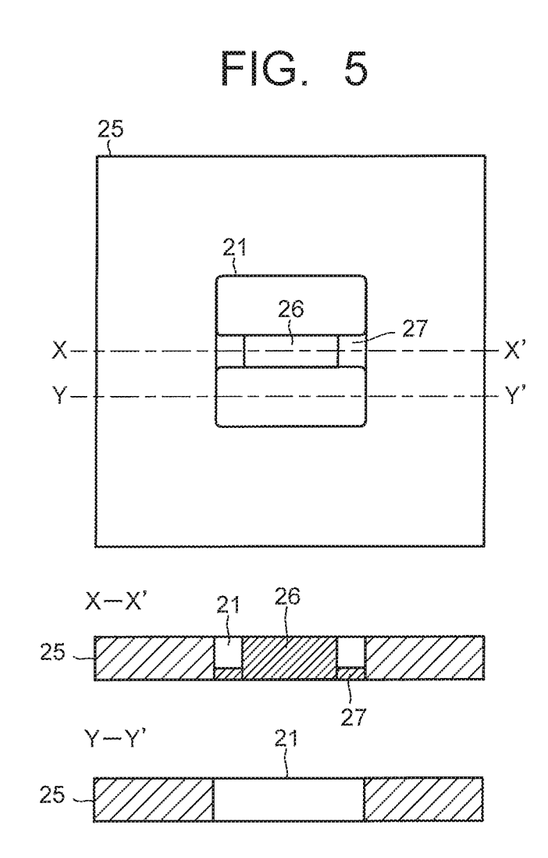
FIG. 5 is a view illustrating the other example of the cathode solution flow path in the electrolysis cell illustrated in FIG. 2.

In the cathode 22, the reduction reaction of $CO_2$ occurs mainly in a portion in contact with the cathode solution. Therefore, to the cathode solution flow path 21, as illustrated in FIG. 4, the opening portion having a large opening area is preferably applied. However, in order to enhance mechanical retention and electrical connectivity, as illustrated in FIG. 5, a land (convex portion) 26 may be provided in the cathode solution flow path 21. The land 26 in the cathode solution flow path 21 is provided in a center portion of the cathode solution flow path 21, and is retained to the second flow path plate 25 by a bridge portion 27 thinner than the land 26 by so as not to prevent the cathode solution in the cathode solution flow path 21 from flowing through. When the land 26 is provided in the cathode solution flow path 21, the number of lands 26 is preferably small in order to reduce cell resistance.

The $CO_2$ gas flow path 23 is constituted by a pit (groove portion/concave portion) provided in a third flow path plate 28. For the third flow path plate 28 constituting the $CO_2$ gas flow path, a material having low chemical reactivity and high conductivity is preferably used. As such a material, the metal material such as Ti or SUS, carbon, or the like can be cited. Note that in each of the first flow path plate 14, the second flow path plate 25, and the third flow path plate 28, an inlet port and an outlet port for a solution or gas, screw holes for tightening, and the like, whose illustrations are omitted, are provided. Further, in front of and behind each of the flow path plates 14, 25, and 28, packing whose illustration is omitted is sandwiched as necessary.

Figure 6:
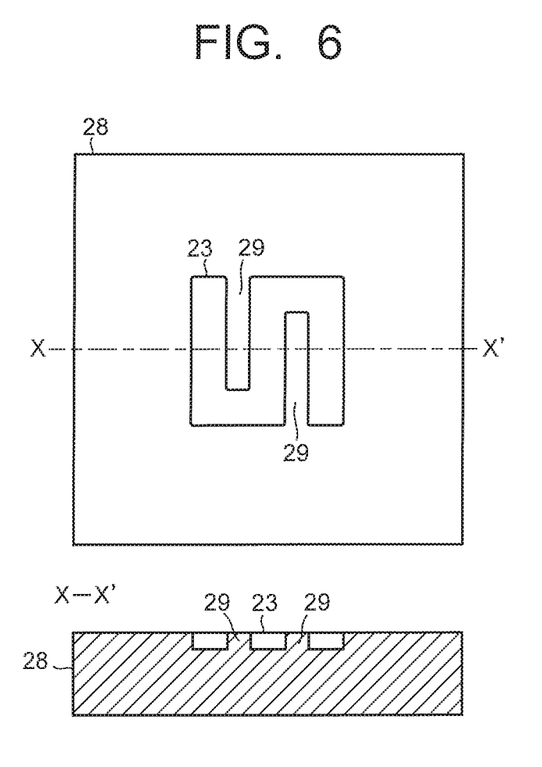
FIG. 6 is a view illustrating one example of a $CO_2$ gas flow path in the electrolysis cell illustrated in FIG. 2.

To the third flow path plate 28, a gas inlet port and a gas outlet port whose illustrations are omitted are connected, and via these gas inlet port and gas outlet port, $CO_2$ gas or gas containing $CO_2$ (sometimes collectively referred to simply as $CO_2$ gas.) is introduced and discharged by the gas supply system 300. The $CO_2$ gas flows through in the $CO_2$ gas flow path 23 so as to be in contact with the cathode 22. Along the $CO_2$ gas flow path 23, as illustrated in FIG. 6, a plurality of lands (convex potions) 29 are preferably provided. The lands 29 are provided for the mechanical retention and the electrical continuity. The lands 29 are preferably provided alternately, and this makes the $CO_2$ gas flow path 23 serpentine similarly to the anode solution flow path 12. The cathode current collector 24 is electrically in contact with a surface on a side opposite to the cathode 22 of the third flow path plate 28.

Figure 7:
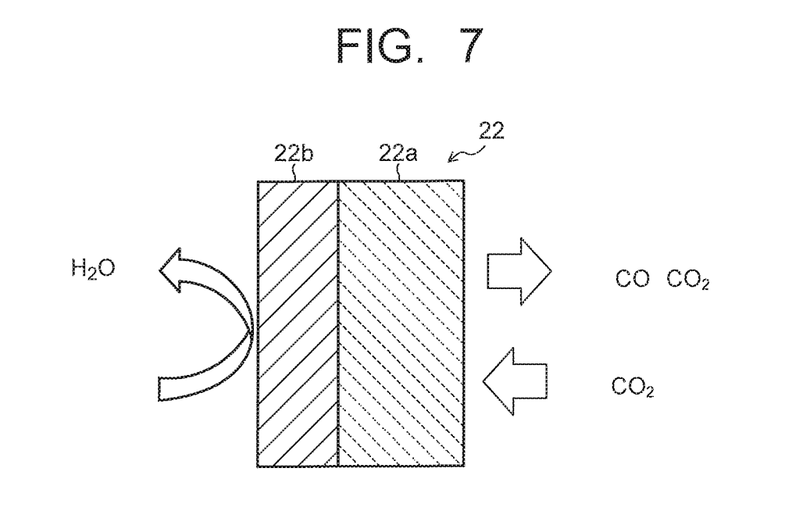
FIG. 7 is a view illustrating one example of a cathode in the electrolysis cell illustrated in FIG. 2.
Figure 8:
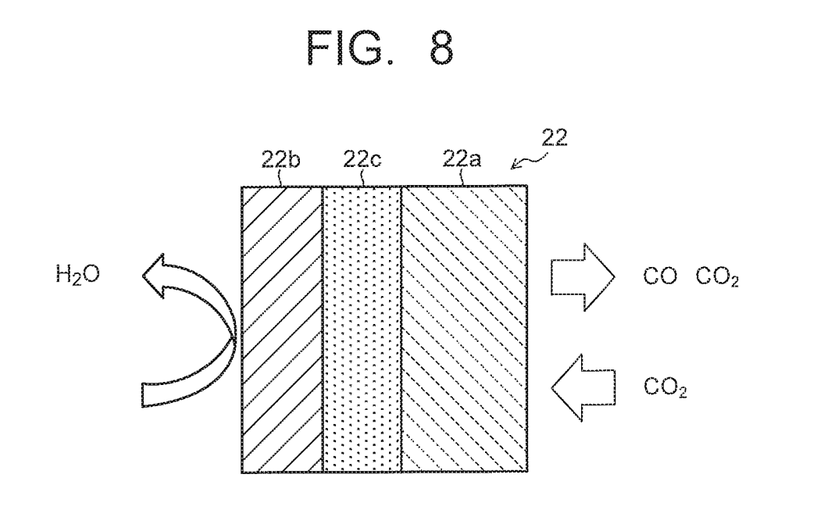
FIG. 8 is a view illustrating the other example of the cathode in the electrolysis cell illustrated in FIG. 2.
Figure 9:
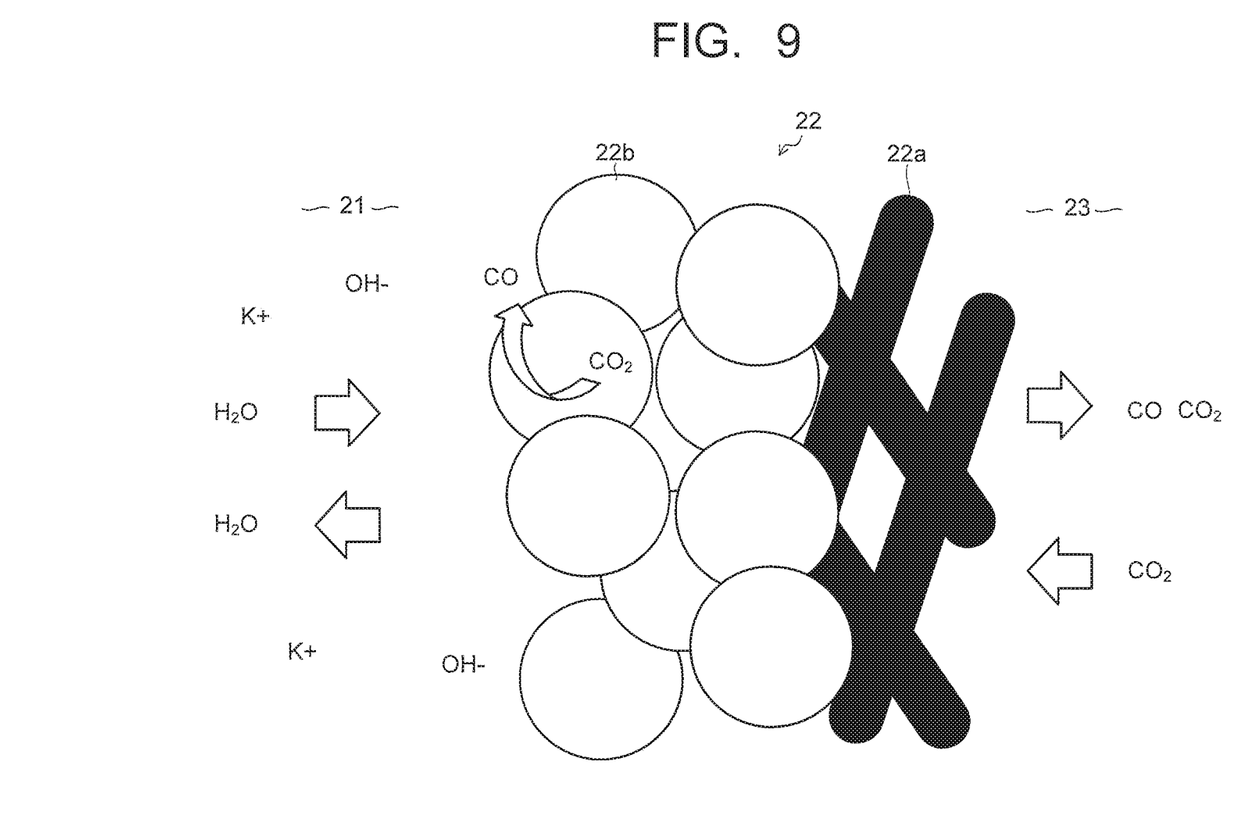
FIG. 9 is a view schematically illustrating a reaction in the cathode in the electrolysis cell illustrated in FIG. 2.

The cathode 22 has a gas diffusion layer 22a and a cathode catalyst layer 22b provided thereon as illustrated in FIG. 7. Between the gas diffusion layer 22a and the cathode catalyst layer 22b, as illustrated in FIG. 8, a porous layer 22c denser than the gas diffusion layer 22a may be disposed. As illustrated in FIG. 9, the gas diffusion layer 22a is disposed on the $CO_2$ gas flow path 23 side, and the cathode catalyst layer 22b is disposed on the cathode solution flow path 21 side. The cathode catalyst layer 22b preferably has catalyst nanoparticles, a catalyst nanostructure, or the like. The gas diffusion layer 22a is constituted by carbon paper, carbon cloth, or the like, for example, and subjected to water repellent treatment. The porous layer 22c is constituted by a porous body whose pore size is smaller than that of the carbon paper or the carbon cloth.

As illustrated in a schematic view in FIG. 9, in the cathode catalyst layer 22b, the cathode solution or ions are supplied and discharged from the cathode solution flow path 21, and in the gas diffusion layer 22a, the $CO_2$ gas is supplied from the $CO_2$ gas flow path 23 and further a product by the reduction reaction of the $CO_2$ gas is discharged. By subjecting the gas diffusion layer 22a to moderate water repellent treatment, the $CO_2$ gas reaches the cathode catalyst layer 22b mainly owing to gas stirring. The reduction reaction of $CO_2$ or the reduction reaction of a carbon compound produced thereby occurs in the vicinity of a boundary between the gas diffusion layer 22a and the cathode catalyst layer 22b, a gaseous product is discharged mainly from the $CO_2$ gas flow path 23, and a liquid product is discharged mainly from the cathode solution flow path 21.

The cathode catalyst layer 22b is preferably constituted of a catalyst material (cathode catalyst material) capable of reducing carbon dioxide to produce a carbon compound and further reducing the carbon compound produced thereby to produce a carbon compound as necessary, and capable of reducing an overvoltage of the above reaction. As such a material, there can be cited a metal such as gold (Au), silver (Ag), copper (Cu), platinum (Pt), palladium (Pd), nickel (Ni), cobalt (Co), iron (Fe), manganese (Mn), titanium (Ti), cadmium (Cd), zing (Zn), indium (In), gallium (Ga), lead (Pb), or tin (Sn), a metal material such as an alloy or an intermetallic compound containing at least one of the above metals, a carbon material such as carbon (C), graphene, CNT (carbon nanotube), fullerene, or ketjen black, or a metal complex such as a Ru complex or a Re complex. To the cathode catalyst layer 22b, various shapes such as a plate shape, a mesh shape, a wire shape, a particle shape, a porous shape, a thin film shape, and an island shape can be applied.

The cathode catalyst material constituting the cathode catalyst layer 22b preferably has nanoparticles of the above-described metal material, a nanostructure of the metal material, nanowires of the metal material, or a composite body in which the nanoparticles of the above-described metal material are supported by a carbon material such as carbon particles, carbon nanotubes, or graphene. Applying catalyst nanoparticles, a catalyst nanostructure, a catalyst nanowire, a catalyst nano-support structure, or the like as the cathode catalyst material makes it possible to enhance reaction efficiency of the reduction reaction of carbon dioxide in the cathode 22.

The separator 30 is constituted of an ion exchange membrane or the like capable of moving ions between the anode 11 and the cathode 22 and separating the anode part 10 and the cathode part 20. As the ion exchange membrane, for example, a cation exchange membrane such as Nafion or Flemion, or an anion exchange membrane such as Neosepta, or Selemion can be used. As described later, when an alkaline solution is used as the anode solution or the cathode solution and it is assumed that hydroxide ions ($OH^-$) move mainly, the separator 30 is preferably constituted of the anion exchange membrane. Also other than the ion exchange membrane, a glass filter, a porous polymeric membrane, a porous insulating material, or the like may be applied to the separator 30 as long as they are a material capable of moving ions between the anode 11 and the cathode 22.

The anode solution and the cathode solution are preferably a solution containing at least water ($H_2O$). Because carbon dioxide ($CO_2$) is supplied from the $CO_2$ gas flow path 23, the cathode solution may contain or need not contain carbon dioxide ($CO_2$). To the anode solution and the cathode solution, the same solution may be applied or different solutions may be applied. As a solution used as the anode solution and the cathode solution and containing $H_2O$, for example, an aqueous solution containing an arbitrary electrolyte can be cited. As the aqueous solution containing the electrolyte, for example, there can be cited an aqueous solution containing at least one ion selected from a hydroxide ion ($OH^-$), a hydrogen ion ($H^+$), a potassium ion ($K^+$), a sodium ion ($Na^+$), a lithium ion ($Li^+$), a chloride ion ($Cl^-$), a bromide ion ($Br^-$), an iodide ion ($I^-$), a nitrate ion ($NO_3^-$), a sulfate ion ($SO_4^{2-}$), a phosphate ion ($PO_4^{2-}$), a borate ion ($BO_3^{3-}$), and a hydrogen carbonate ion ($HCO_3^-$). In order to reduce electrical resistance of the solution, as the anode solution and the cathode solution, an alkaline solution in which an electrolyte such as a potassium hydroxide or a sodium hydroxide is dissolved in high concentration is preferably used.

For the cathode solution, an ionic liquid which is made of salts of cations such as imidazolium ions or pyridinium ions and anions such as $BF_4^-$ or $PF_6^-$ and which is in a liquid state in a wide temperature range, or its aqueous solution may be used. As another cathode solution, there can be cited an amine solution of ethanolamine, imidazole, pyridine, or the like, or an aqueous solution thereof. As amine, any of primary amine, secondary amine, and tertiary amine is applicable.

To the anode solution flow path 12 of the anode part 10, the anode solution is supplied from the anode solution supply system 100. The anode solution supply system 100 circulates the anode solution so that the anode solution flows through in the anode solution flow path 12. The anode solution supply system 100 has a pressure control unit 101, an anode solution tank 102, a flow rate control unit (pump) 103, a reference electrode 104, and a pressure gauge 105, and is constituted so that the anode solution circulates in the anode solution flow path 12. The anode solution tank 102 is connected to a gas component collection unit which collects a gas component such as oxygen ($O_2$) contained in the circulating anode solution and is not illustrated. The anode solution, whose flow rate and pressure are controlled in the pressure control unit 101 and the flow rate control unit 103, is introduced to the anode solution flow path 12.

To the cathode solution flow path 21 of the cathode part 20, the cathode solution is supplied from the cathode solution supply system 200. The cathode solution supply system 200 circulates the cathode solution so that the cathode solution flows through in the cathode solution flow path 21. The cathode solution supply system 200 has a pressure control unit 201, a cathode solution tank 202, a flow rate control unit (pump) 203, a reference electrode 204, and a pressure gauge 205, and is constituted so that the cathode solution circulates in the cathode solution flow path 21. The cathode solution tank 202 is connected to a gas component collection unit 206 which collects a gas component such as carbon monoxide (CO) contained in the circulating cathode solution. The cathode solution, whose flow rate and pressure are controlled in the pressure control unit 201 and the flow rate control unit 203, is introduced to the cathode solution flow path 21.

To the $CO_2$ gas flow path 23, the $CO_2$ gas is supplied from the gas supply system 300. The gas supply system 300 has a $CO_2$ gas cylinder 301, a flow rate control unit 302, a pressure gauge 303, and a pressure control unit 304. The $CO_2$ gas, whose flow rate and pressure are controlled in the flow rate control unit 302 and the pressure control unit 304, is introduced to the $CO_2$ gas flow path 23. The gas supply system 300 is connected to the product collection system 400 which collects a product in gas which has flowed through the $CO_2$ gas flow path 23. The product collection system 400 has a gas/liquid separation unit 401 and a product collection unit 402. A reduction product such as CO or $H_2$ contained in the gas which has flowed through the $CO_2$, gas flow path 23 is accumulated via the gas/liquid separation unit 401 in the product collection unit 402.

Part of the reduction product accumulated in the product collection unit 402 is sent to a reduction performance detection unit 501 of the product control system 500. In the reduction performance detection unit 501, a production amount and a proportion of each product such as CO or $H_2$ in the reduction product are detected. The detected production amount and proportion of each product are inputted to a data collection control unit 502 of the product control system 500. The data collection control unit 502 is electrically connected via bi-directional signal lines whose illustration is partially omitted to the pressure control unit 101 and the flow rate control unit 103 of the anode solution supply system 100, the pressure control unit 201 and the flow rate control unit 203 of the cathode solution supply system 200, and the flow rate control unit 302 and the pressure control unit 304 of the gas supply system 300 in addition to the reduction performance detection unit 501.

Each operation of the electrolysis cell 2, the power supply 40, the anode solution supply system 100, the cathode solution supply system 200, and the gas supply system 300 is controlled by the data collection control unit 502. That is, the data collection control unit 502 controls the pressure control unit 201 of the cathode solution supply system 200 and the pressure control unit 304 of the gas supply system 300 so as to adjust the production amount and the proportion of each product detected in the reduction performance detection unit 501, specifically so that the production amount and the proportion of each product each become a desired value. Thereby, a differential pressure between a pressure of the cathode solution flowing through the cathode solution flow path 21 and a pressure of the $CO_2$ gas flowing through the $CO_2$ gas flow path 23 is controlled. Because the differential pressure between the pressure of the cathode solution and the pressure of the $CO_2$ gas affects the production amount and the proportion of each product, controlling the differential pressure based on a detection result of the reduction product makes it possible to adjust the production amount and the proportion of each product in a desired state.

When the differential pressure between the pressure of the cathode solution and the pressure of the $CO_2$ gas is too large, there is a possibility that the $CO_2$ gas permeates the cathode solution flow path 21 or the cathode solution permeates the $CO_2$ gas flow path 23. Both of these become a factor of impairing the reduction reaction of $CO_2$ in the cathode 22. Therefore, an absolute value of the differential pressure between the pressure of the cathode solution and the pressure of the $CO_2$ gas is preferably set to 100 kPa or less. Further, when the absolute value of the differential pressure between the pressure of the cathode solution and the pressure of the $CO_2$ gas is too small, a function of adjusting the production amount and the proportion of each product decreases, and therefore the absolute value of the differential pressure is preferably 0.1 kPa or more. The absolute value of the differential pressure is more preferably 0.1 kPa or more to 10 kPa or less. Specific control contents of the differential pressure between the pressure of the cathode solution and the pressure of the CO₂ gas will be described later.

Next, an operation of the carbon dioxide electrolytic device 1 of the embodiment will be described. Here, a case of producing carbon monoxide (CO) as the carbon compound is mainly described, but the carbon compound as the reduction product of carbon dioxide is not limited to carbon monoxide. The carbon compound may be methane ($CH_4$), ethane ($C_2H_6$), ethylene ($C_2H_4$), methanol ($CH_3OH$), ethanol ($C_2H_5OH$), ethylene glycol ($C_2H_6O_2$), or the like as described above, and further carbon monoxide which is the reduction product may be further reduced to produce the organic compounds as described above. Further, as a reaction process by the electrolysis cell 2, a case of mainly producing hydrogen ions ($H^+$) and a case of mainly producing hydroxide ions ($OH^-$) are considered, but it is not limited to either of these reaction processes.

First, the reaction process in a case of mainly oxidizing water ($H_2O$) to produce hydrogen ions ($H^+$) is described. When an electric current is supplied from the power supply 40 between the anode 11 and the cathode 22, the oxidation reaction of water ($H_2O$) occurs in the anode 11 in contact with the anode solution. Specifically, as indicated by the following (1) formula, $H_2O$ contained in the anode solution is oxidized and oxygen ($O_2$) and hydrogen ions ($H^+$) are produced.

$$2H_2O \rightarrow 4H^+ + O_2 + 4e^- \qquad (1)$$

$H^+$ produced in the anode 11 moves in the anode solution existing in the anode 11, the separator 30, and the cathode solution in the cathode solution flow path 21 and reaches the vicinity of the cathode 22. The reduction reaction of carbon dioxide ($CO_2$) occurs by electrons ($e^-$) based on the electric current which is supplied from the power supply 40 to the cathode 22 and $H^+$ which moves to the vicinity of the cathode 22. Specifically, as indicated by the following (2) formula, $CO_2$ supplied from the $CO_2$ gas flow path 23 to the cathode 22 is reduced and CO is produced.

$$2CO_2 + 4H^+ + 4e^- \rightarrow 2CO + 2H_2O \qquad (2)$$

Next, the reaction process in a case of mainly reducing carbon dioxide ($CO_2$) to produce hydroxide ions ($OH^-$) is described. When an electric current is supplied from the power supply 40 between the anode 11 and the cathode 22, in the vicinity of the cathode 22, as indicated by the following (3) formula, water ($H_2O$) and carbon dioxide ($CO_2$) are reduced and carbon monoxide (CO) and hydroxide ions ($OH^-$) are produced. The hydroxide ions ($OH^-$) diffuse in the vicinity of the anode 11, and as indicated by the following (4) formula, the hydroxide ions ($OH^-$) are oxidized and oxygen ($O_2$) is produced.

$$2CO_2 + 2H_2O + 4e^- \rightarrow 2CO + 4OH^- \qquad (3)$$

$$4OH^- \rightarrow 2H_2O + O_2 + 4e^- \qquad (4)$$

In the above-described reaction processes in the cathode 22, the reduction reaction of $CO_2$ is considered to occur in the vicinity of the boundary between the gas diffusion layer 22a and the cathode catalyst layer 22b as described above. At this time, when the pressure of the cathode solution flowing through the cathode solution flow path 21 is larger than the pressure of the $CO_2$ gas flowing through the $CO_2$ gas flow path 23, production of $H_2$ by the reduction reaction of $H_2O$ in the cathode solution sometimes has superiority to production of CO by the reduction reaction of $CO_2$. In the above case, the production amount and the proportion of $H_2$ in the reduction product increase and the production amount and the proportion of intended CO decrease. In such a case, the differential pressure is adjusted by the data collection control unit 502 functioning as a differential pressure control unit so that the pressure of the $CO_2$ gas is larger than the pressure of the cathode solution, thereby making the reduction reaction of $CO_2$ preferentially occur in the vicinity of the boundary between the gas diffusion layer 22a and the cathode catalyst layer 22b. This makes it possible to increase the production amount and the production proportion of CO by the reduction reaction of $CO_2$. The specific differential pressure is preferably 0.1 kPa or more to 100 kPa or less, and more preferably 0.1 kPa or more to 10 kPa or less as described above.

As described above, the differential pressure between the pressure of the cathode solution flowing through the cathode solution flow path 21 and the pressure of the $CO_2$ gas flowing through the $CO_2$ gas flow path 23 is preferably adjusted so that the pressure of the $CO_2$ gas is larger than the pressure of the cathode solution. However, this is not necessarily restrictive. For example, when the gas diffusion layer 22a has high water repellency and the cathode solution does not easily enter the gas diffusion layer 22a, or when the $CO_2$ gas easily leaks to the cathode catalyst layer 22b side, an adjustment may be made so that the pressure of the cathode solution is larger than the pressure of the $CO_2$ gas. In both cases, since the differential pressure between the pressure of the cathode solution and the pressure of the $CO_2$ gas affects the production amount and the proportion of each product, the differential pressure is adjusted so that they each become a desired value, based on the production amount and the proportion of each product detected in the reduction performance detection unit 501. This makes it possible to obtain the reduction product having desired production amount and proportion.

Further, in both of the above-described reaction process in which hydrogen ions ($H^+$) are mainly produced and reaction process in which hydroxide ions ($OH^-$) are mainly produced, oxygen ($O_2$) is produced in the anode 11. At this time, for example, in a cell structure in which a separator is sandwiched by a cathode solution flow path and an anode solution flow path, air bubbles of oxygen ($O_2$) gas which occur in the anode 11 stay in the anode solution flow path, and cell resistance between the anode and the separator (ion exchange membrane or the like) increases, and thereby a voltage variation of the anode is considered to become large. In contrast to this, in the electrolysis cell 2 of the embodiment, the anode solution flow path 12 is not disposed between the anode 11 and the separator 30, and the anode 11 and the separator 30 are brought in close contact with each other, and therefore oxygen gas which occurs in the anode 11 is discharged to the anode solution flow path 12 together with the anode solution. Therefore, it is possible to prevent the oxygen gas from staying between the anode 11 and the separator 30. Accordingly, it becomes possible to suppress a variation in a cell voltage due to the voltage variation of the anode.

Moreover, in the electrolysis cell 2 of the embodiment, providing the lands 15 and the lands 29 along the anode solution flow path 12 and the $CO_2$ gas flow path 23 makes it possible to increase a contact area between the anode 11 and the first flow path plate 14 constituting the anode solution flow path 12 and a contact area between the cathode 22 and the third flow path plate 28 constituting the $CO_2$ gas flow path 23. Further, providing the land 26 in the cathode solution flow path 21 makes it possible to increase a contact area between the cathode 22 and the second flow path plate 25 constituting the cathode solution flow path 21. These make electrical continuity between the anode current collector 13 and the cathode current collector 24 good while enhancing mechanical retentivity of the electrolysis cell 2, and make it possible to improve reduction reaction efficiency of $CO_2$, or the like.

EXAMPLE

Next, an example and its evaluation result will be described.

Example 1

An electrolytic device illustrated in FIG. 1 and FIG. 2 was fabricated as follows, and electrolysis performance of carbon dioxide was examined. First, on carbon paper on which a porous layer was provided, a cathode to which gold nanoparticle-supported carbon particles were applied was produced by the following process. A coating solution in which the gold nanoparticle-supported carbon particles and pure water, a Nafion solution, and ethylene glycol were mixed was produced. An average particle diameter of the gold nanoparticle was 8.7 nm, and a supported amount thereof was 18.9 mass %. An air brush was filled with this coating solution, spray coating was performed using Ar gas on the carbon paper on which the porous layer was provided. Flowing water washing was performed by pure water for 30 minutes after the coating, and thereafter organic matter such as ethylene glycol was removed by oxidation through immersing in a hydrogen peroxide solution. This was cut into a size of 2×2 cm to be set as the cathode. Note that a coating amount of Au was estimated at about 0.2 mg/cm$^2$ from a mixing amount of the gold nanoparticles and the carbon particles in the coating solution.

For an anode, an electrode in which $IrO_2$ nanoparticles which became a catalyst were applied to Ti mesh was used. As the anode, the one in which $IrO_2$/Ti mesh was cut into 2×2 cm was used.

The electrolysis cell 2 was produced by being stacked in order of the cathode current collector 24, the $CO_2$ gas flow path 23 (the third flow path plate 28), the cathode 22, the cathode solution flow path 21 (the second flow path plate 25), the separator 30, the anode 11, the anode solution flow path 12 (the first flow path plate 14), and the anode current collector 13 from the top, being sandwiched by the support plates not illustrated, and further being tightened by the bolts, as illustrated in FIG. 2. For the separator 30, an anion exchange membrane (brand name: Selemion, manufactured by ASAHI GLASS CO., LTD.) was used. The $IrO_2$/Ti mesh of the anode 11 was brought in close contact with the anion exchange membrane. A thickness of the cathode solution flow path 21 was set to 1 mm. Note that an evaluation temperature was set to room temperature.

The electrolytic device illustrated in FIG. 1 was operated under the following condition. $CO_2$ gas was supplied to the $CO_2$ gas flow path of the electrolysis cell at 20 sccm, an aqueous potassium hydroxide solution (concentration 1 M KOH) was introduced to the cathode solution flow path at a flow rate of 5 mL/min, and the aqueous potassium hydroxide solution (concentration 1 M KOH) was introduced to the anode solution flow path at a flow rate of 20 mL/min. A differential pressure between the $CO_2$ gas and the cathode solution was controlled so that a pressure of the $CO_2$ gas was 2.5 kPa larger than a pressure of the cathode solution, so as to adjust a proportion of a reduction product. Next, a 600 mA constant current (constant current density 150 mA/cm$^2$) was passed between the anode and the cathode using the power supply, an electrolytic reaction of $CO_2$ was performed, and a cell voltage, an anode potential, and a cathode potential at that time were measured. Note that a Hg/HgO reference electrode (+0.098 V vs. SHE) was used for potential measurement, and pH was set to 13.65 to calculate an overvoltage. Part of gas outputted from the $CO_2$ gas flow path was collected, and production amounts of CO gas to be produced by a reduction reaction of $CO_2$ and $H_2$ gas to be produced by a reduction reaction of water were analyzed by a gas chromatograph. From these gas production amounts, a partial current density and Faraday's efficiency which is a ratio between the entire current density and the partial current density of CO or $H_2$ were calculated.

Figure 10:
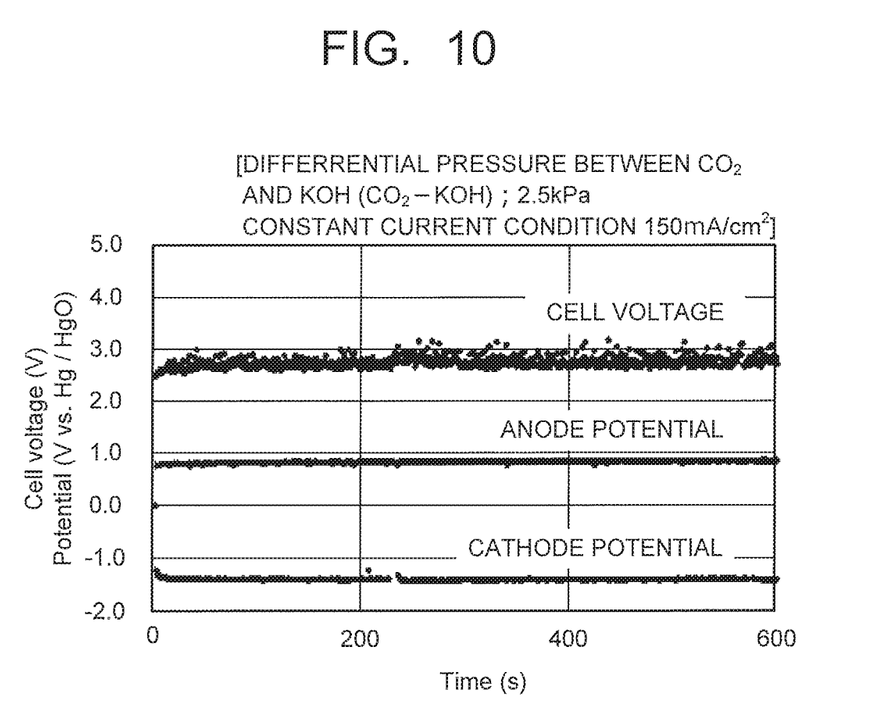
FIG. 10 is a chart illustrating time changes in a cell voltage, an anode potential, and a cathode potential by using a carbon dioxide electrolytic device in an example.

FIG. 10 illustrates time changes in the cell voltage, the anode potential, and the cathode potential. Table 1 presents an average value of the cell voltage, an anode overvoltage, and a cathode overvoltage between 300 seconds and 570 seconds when gas collection is performed, and the Faraday's efficiency, the partial current density, and electrolysis efficiency of CO and $H_2$. As presented in Table 1, good electrolysis performance having high selectivity of CO, such as 2.76 V in the cell voltage, 83% in the Faraday's efficiency of CO, and 40% in the electrolysis efficiency of CO, was obtained.

TABLE 1

| EXAMPLE 1 | |
|---|---|
| CELL VOLTAGE [V]* | 2.76 |
| ANODE OVERVOLTAGE [V]* | 0.53 |
| CATHODE OVERVOLTAGE [V]* | 0.39 |
| CO FARADAY'S EFFICIENCY [%] | 83 |
| $H_2$ FARADAY'S EFFICIENCY [%] | 13 |
| CO PARTIAL CURRENT DENSITY [mA/cm$^2$] | 125 |
| $H_2$ PARTIAL CURRENT DENSITY [mA/cm$^2$] | 15.8 |
| ELECTROLYSIS EFFICIENCY OF CO [%] | 40 |
| ELECTROLYSIS EFFICIENCY OF $H_2$ [%] | 5.6 |
| ELECTROLYSIS EFFICIENCY OF CO AND $H_2$ [%] | 46 |

*AVERAGE VALUE OF 300 s TO 570 s.

Reference Example 1

An electrolytic reaction of $CO_2$ was performed similarly to Example 1 except that the differential pressure between the $CO_2$ gas and the cathode solution was changed, and performance was evaluated. The differential pressure between the $CO_2$ gas and the cathode solution was controlled at −0.6 kPa under a condition in which the pressure of the cathode solution was larger. Table 2 presents each of performance values found similarly to Example 1. As presented in Table 2, low selectivity and low electrolysis efficiency of CO as compared with Example 1, such as 3.12 V in the cell voltage, 21% in the Faraday's efficiency of CO, and 9% in the electrolysis efficiency of CO were confirmed. From these results, it was confirmed that improvement in the selectivity and the electrolysis efficiency of CO was achieved by controlling the differential pressure between the $CO_2$ gas and the cathode solution.

TABLE 2

| REFERENCE EXAMPLE 1 | |
|---|---|
| CELL VOLTAGE [V]* | 3.12 |
| ANODE OVERVOLTAGE [V]* | 0.51 |
| CATHODE OVERVOLTAGE [V]* | 0.43 |

TABLE 2-continued

REFERENCE EXAMPLE 1

| | |
|---|---|
| CO FARADAY'S EFFICIENCY [%] | 21 |
| $H_2$ FARADAY'S EFFICIENCY [%] | 25 |
| CO PARTIAL CURRENT DENSITY [mA/cm$^2$] | 31 |
| $H_2$ PARTIAL CURRENT DENSITY [mA/cm$^2$] | 31.2 |
| ELECTROLYSIS EFFICIENCY OF CO [%] | 9 |
| ELECTROLYSIS EFFICIENCY OF $H_2$ [%] | 9.9 |
| ELECTROLYSIS EFFICIENCY OF CO AND $H_2$ [%] | 19 |

*AVERAGE VALUE OF 300 s TO 570 s.

Note that configurations of the above-described embodiments may be each applied in combination, and further may be partially substituted. Herein, while certain embodiments of the invention have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the invention.

What is claimed is:

1. A method for electrolyzing carbon dioxide, comprising:
supplying carbon dioxide to a carbon dioxide supply flow path in an electrolysis cell, supplying a cathode solution to a cathode solution flow path in the electrolysis cell, and supplying an anode solution to an anode solution flow path in the electrolysis cell, the electrolysis cell having an anode, a cathode, the carbon dioxide supply flow path which supplies the carbon dioxide to the cathode, the cathode solution flow path which supplies the cathode solution to the cathode, the anode solution flow path which supplies the anode solution to the anode, and a separator to separate the anode and the cathode;
supplying an electric current from a power supply connected to the anode and the cat ode, to reduce the carbon dioxide and thus produce a carbon compound in a vicinity of the cathode, and to oxidize water or hydroxide ions and thus produce oxygen in a vicinity of the anode:
detecting a production amount of the carbon compound produced by a reduction reaction in the cathode; and
controlling a differential pressure between a pressure of the cathode solution and a pressure or the carbon dioxide so as to adjust the production amount of the detected carbon compound,
wherein the cathode has a gas diffusion layer disposed so as to contact with the carbon dioxide flowing in the carbon dioxide supply flow path, a cathode catalyst layer disposed so as to contact with the cathode solution flowing in the cathode solution flow path, and a porous layer which has a pore size smaller than that of the gas diffusion layer, and is disposed between the gas diffusion layer and the cathode catalyst layer,
wherein the cathode catalyst layer contains at least one selected from the group consisting of gold, silver, copper, platinum, palladium, nickel, cobalt, iron, manganese, titanium, cadmium, zinc, indium, gallium, and lead, and
wherein the differential pressure is controlled so that the pressure of the carbon dioxide flowing in the carbon dioxide supply flow path is larger than the pressure of the cathode solution flowing in the cathode solution flow path, and the differential pressure is 0.1 kPa more to 10 kPa or less.

2. The method according to claim 1, wherein
the carbon dioxide is reduced to produce the carbon compound while water is reduced to produce hydrogen M the vicinity of the cathode, and
the differential pressure is controlled so that a reduction reaction of the carbon dioxide preferentially occurs than a reduction reaction of the water.

3. The method according to claim 1, wherein
the carbon dioxide is reduced to produce carbon monoxide while water is reduced to produce hydrogen in the vicinity of the cathode, and
the differential pressure is controlled so that Faraday's efficiency of the carbon monoxide is larger than Faraday's efficiency of the hydrogen.

4. The method according to claim 1, wherein
the cathode has a first surface facing the cathode solution flow path and a second surface facing the carbon dioxide supply flow path, and the cathode solution flow path is disposed between the separator and the cathode so that the cathode solution is in contact with the separator and the cathode.

5. The method according to claim 1, wherein
the anode solution and the cathode solution contain at least one ion selected from the group consisting of a hydroxide ion, a hydrogen ion, a potassium ion, a sodium ion, a lithium a chloride ion, a bromide ion, an iodide ion, a nitrate ion, a sulfate ion, a phosphate ion, a borate ion, and a hydrogen carbon ion.

6. The method according to claim 1, wherein
the carbon compound to be produced by a reduction reaction of the carbon dioxide contains at least one selected from the group consisting of carbon monoxide, methane, ethane, ethylene, methanol, ethanol, and ethylene glycol.

7. The method according to claim 1, wherein
the carbon dioxide supply flow path has a gas inlet port connected to a carbon dioxide supply unit and a gas outlet port connected to a product collection unit collecting a reduction product which is produced b the cathode.

* * * * *